(12) United States Patent
Kobayashi et al.

(10) Patent No.: US 7,236,621 B2
(45) Date of Patent: Jun. 26, 2007

(54) DIAGNOSIS SUPPORTING DEVICE

(75) Inventors: Hiroyuki Kobayashi, Saitama-ken (JP); Noriko Ota, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 756 days.

(21) Appl. No.: 10/663,788

(22) Filed: Sep. 17, 2003

(65) Prior Publication Data
US 2004/0064016 A1     Apr. 1, 2004

(30) Foreign Application Priority Data
Sep. 30, 2002    (JP)    ............ P2002-287034

(51) Int. Cl.
*G06K 9/00*   (2006.01)
(52) U.S. Cl. ................. 382/128; 348/70
(58) Field of Classification Search .......... 382/128; 600/118, 160, 109, 476; 348/70
See application file for complete search history.

(56) References Cited
U.S. PATENT DOCUMENTS 6,371,908 B1 * 4/2002 Furusawa et al. .......... 600/160
6,537,211 B1 * 3/2003 Wang et al. ............... 600/178
7,050,086 B2 * 5/2006 Ozawa ....................... 348/70

FOREIGN PATENT DOCUMENTS

| JP | 2000-23903 | 1/2000 |
| JP | 2002-500907 | 1/2002 |
| WO | 99/37204 | 7/1999 |

\* cited by examiner

*Primary Examiner*—Joseph Mancuso
*Assistant Examiner*—Nancy Bitar
(74) *Attorney, Agent, or Firm*—Greenblum & Bernstein, P.L.C.

(57) ABSTRACT

Disclosed is a diagnosis supporting system that acquires a reference image signal of a subject that is illuminated with visible light and a fluorescent image signal of the subject that is excited by irradiation with excitation light, calculates a difference between brightness level of a pixel in the reference image signal and brightness level of a pixel in the fluorescent image signal at the corresponding position for all of target pixels and generates an observation image signal by converting the pixels in the reference image signal whose differences are larger than a predetermined value into red pixels. In the case of high contrast, all of the pixels become target pixels to be processed. In the case of low contrast, the number of the target pixels is reduced to ¼ of all the pixels.

16 Claims, 7 Drawing Sheets

DIAGNOSIS SUPPORTING DEVICE

BACKGROUND OF THE INVENTION

The present invention relates to a diagnosis supporting device for generating an image signal of an image of a subject used in a diagnosis of living tissue.

Irradiation of light at a specific wavelength excites living tissue, which causes a living tissue to emit fluorescence. Further, intensity of fluorescence emitted from abnormal living tissue that is suffering from a lesion such as a tumor or cancer is smaller than that emitted from normal living tissue.

Japanese Patent Laid-open publication No. 2000-023903 discloses a diagnosis supporting device that finds abnormality of an inner wall of a body cavity (a body cavity wall) such as gullet or stomach and specifies the position of the abnormality based on such a principle.

The diagnosis supporting device disclosed in the publication operates together with an existing video endoscope system that electronically captures images guided by an endoscope to display the images on a monitor.

The diagnosis supporting device is provided with a probe consisting of a number of optical fibers bundled up, a light source for alternatively supplying visible light and excitation light to the proximal end surface of the probe and an image processing circuit for providing images captured by the video endoscope system with a predetermined processing to output the processed image signals on a monitor.

When the diagnosis supporting device is used, the distal end of the video endoscope is inserted into a body cavity and then, the probe is led through a forceps channel of the video endoscope so that the tip end the probe is exposed in the body cavity. Visible light and excitation light alternatively illuminate a body cavity through the probe, and the illuminated body cavity is captured by a camera mounted on the distal end of the video endoscope.

Then, an illuminating/processing device of the video endoscope system outputs an image signal of an image when body cavity wall is illuminated by visible light (a reference image signal) and an image signal of an image when excited body cavity wall emits fluorescence (a fluorescent image signal).

The image processing circuit executes the following processes whenever one set of a reference image signal and a fluorescent image signal are acquired. That is, the image processing circuit extracts the maximum brightness levels and the minimum brightness levels from all pixels of the reference image signal and the fluorescence image signal, respectively.

Next, the image processing circuit standardizes the reference image signal and the fluorescence image signal by converting a value of a pixel having the maximum brightness level into a predetermined maximum gradation, a value of a pixel having the minimum brightness level into a predetermined minimum gradation and values of other pixels having intermediate brightness levels into corresponding gradations.

Next, the image processing circuit calculates difference between gradations of the standardized reference image signal and the standardized fluorescent image signal at the same coordinate (difference obtained by subtracting gradation at the predetermined coordinate in the standardized fluorescent image signal from gradation at the same coordinate in the standardized reference image signal) for every coordinate. Then, the image processing circuit creates a new binary image signal. A coordinate in the binary image signal corresponds to coordinates in each of the reference image signal and the fluorescent image signal. When a difference at a predetermined coordinate is equal to or larger than a predetermined threshold value, the value at the same coordinate in the binary image signal becomes "1". On the other hand, when a difference at a predetermined coordinate is smaller than the threshold value, the value at the same coordinate in the binary image signal becomes "0".

Next, the image processing circuit converts the reference image signal to a monochromatic RGB image signal and then creates a new RGB image signal (an observation image signal) by converting monochromatic pixels in the monochromatic RGB image signal whose coordinates are coincident with coordinates exhibiting value "1" in the binary image signal into red pixels.

The image processing circuit generates observation image signals according to the above-described processes, storing them into a buffer sequentially. Then, the image processing circuit reads an observation image signal recorded in the buffer to convert it into a NTSC video signal or a PAL video signal as an output signal to a monitor.

Therefore, an operator who performs an operation on a subject with using the diagnosis supporting device can specify an outline and unevenness of body cavity wall by a monochrome part in the observation image signal displayed on the monitor.

Further, the operator can specify maculate red parts and/or block red parts as an agmina of living tissue that emits relatively low fluorescence, i.e., parts that have high risk to be suffering from a lesion such as a tumor or cancer.

However, since the conventional diagnosis supporting device executes the above described complicated processes, the processing speed to generate the observation image signal and to record it into the buffer becomes relatively slow (10 frames per second). Therefore, there is the following inconvenience.

When a taking area of a video endoscope changes while body cavity wall is observed, the processing speed may be insufficient for change of the taking area.

For example, when the video endoscope cannot focus on body cavity wall or when image signal is overexposed because the tip end of the endoscope is too close to the body cavity wall, contrast of a monochromatic part in an observation image signal (a reference image signal) may extremely deteriorate. In such a case, since an outline and unevenness of body cavity wall become uncertain, an operator cannot specify which part in the body cavity wall is indicated by a red part in the observation image signal, which disturbs a diagnosis of living tissue.

At this moment, when the operator moves the tip of the video endoscope to focus on the body cavity wall, indication of observation image signals does not catch up with movement. As a result, the operator loses sight of an attention part, which causes operation delay.

SUMMARY OF THE INVENTION

It is therefore an object of the present invention to provide an improved diagnosis supporting device that is capable of increasing a processing speed so that indication of an observation image signal catch up with movement of the tip of a video endoscope.

A diagnosis supporting device of the present invention is connected to a processor device that acquires an image signal of an image of a subject formed at the tip of an endoscope to convert the image signal into an output video signal for a monitor.

A diagnosis supporting device according to a first aspect of the present invention includes an image signal acquiring section that repeatedly acquires a reference image signal (representing an image of a subject that is illuminated with visible light) and a fluorescent image signal (representing an image of said subject that is excited by irradiation with excitation light to emit fluorescence) transmitted from the processor device; an observation image signal generating section that counts the number of pixels having the maximum brightness level in the reference image signal whenever the image signal acquiring section acquires a set of the reference image signal and the fluorescent image signal, then that calculates a difference between brightness level of a pixel in the reference image signal and brightness level of a pixel in the fluorescent image signal at the corresponding position for all of the pixels in the reference image signal when the number of counted pixels is not larger than a predetermined threshold number or for a part of the pixels selected from the reference image signal when the number of counted pixels is larger than the threshold number, and that generates an observation image signal by converting the pixels in the reference image signal whose differences are larger than a predetermined value into specific pixels exhibiting a predetermined color; a memory section that stores the observation image signal and updates it whenever the observation image signal generating section generates an observation image signal; and an output section that reads the observation image signal stored in the memory section and that converts the observation image signal into an output video signal.

With this construction, when the number of pixels having the maximum brightness level in the reference image signal is larger than the threshold number, the number of target pixels for calculating the differences is reduced, which shorten a time required for differential process.

As a result, while the resolution of the observation image signal falls, the speed for generating the observation image signal increases.

When the number of pixels having the maximum brightness level exceeds the threshold number, it can be judged that the endoscope does not focus on the subject to deteriorate the contrast. That is, the tip of the endoscope should be moved to bring the subject in focus.

In such a case, since a part of the pixels are used as the target pixels, the speed for generating the observation image signal increases, which enables to display the observation image signal on a monitor in real time during the movement. Therefore, an operator has little possibility to lose sight of an attention part.

On the contrary, when the number of pixels having the maximum value in the reference image signal does not exceed the threshold number, it can be judged that the endoscope focuses on the subject with high contrast.

In such a case, since all of the pixels are used as target pixels for calculating the differences, the resolution increases while the speed for generating the observation image signal decreases, which enables detail observation of the subject by the operator.

Further, a diagnosis supporting device according to a second aspect of the present invention includes an information register that registers information representing a first condition or information representing a second condition; an image signal acquiring section that repeatedly acquires the reference image signal and the fluorescent image signal transmitted from the processor device; an observation image signal generating section that determines whether the information registered in the information register represents the first condition or the second condition whenever the image signal acquiring section acquires a set of the reference image signal and the fluorescent image signal, then that calculates a difference between brightness level of a pixel in the reference image signal and brightness level of a pixel in the fluorescent image signal at the corresponding position for all of the pixels in the reference image signal when the information representing the first condition is registered or for a part of the pixels selected from the reference image signal when the information representing the second condition is registered, and that generates an observation image signal by converting the pixels in the reference image signal whose differences are larger than a predetermined value into specific pixels exhibiting a predetermined color; a condition deciding section that registers the information representing the first condition in the information register when the number of the specific pixels exceeds a threshold number and registers the information representing the second condition in the information register when the number of the specific pixels does not exceed the threshold number; a memory section that stores the observation image signal and updates it whenever the observation image signal generating section generates an observation image signal; and an output section that reads the observation image signal stored in the memory section and that converts the observation image signal into an output video signal.

With this construction, when the number of the specific pixels is smaller than the threshold number, the number of target pixels for calculating the differences is reduced, which shorten a time required for differential process.

On the contrary, when the number of the specific pixels exceed the threshold value, all of the pixels are used as target pixels for calculating the differences, which increases the resolution of the observation image signal.

The number of specific pixels varies according to a ratio of affected area. Therefore, the diagnosis supporting system of the second aspect is capable of showing an observation image signal with high resolution when diseased tissue is observed and of showing an observation image signal in real time during movement of the tip of the endoscope when normal tissue is observed.

A diagnosis supporting device according to a third aspect of the present invention includes an image signal acquiring section that repeatedly acquires the reference image signal and the fluorescent image signal transmitted from the processor device; an observation image signal generating section that counts the number of pixels having the maximum brightness level in the reference image signal whenever the image signal acquiring section acquires a set of the reference image signal and the fluorescent image signal, that calculates, when the number of counted pixels is not larger than a predetermined threshold number, a difference between brightness level of a pixel in the reference image signal and brightness level of a pixel in the fluorescent image signal at the corresponding position for all of the pixels in the reference image signal and generates an observation image signal by converting the pixels in the reference image signal whose differences are larger than a predetermined value into specific pixels exhibiting a predetermined color, and that divides, when the number of counted pixels is larger than the threshold number, all pixels in both of the reference image signal and the fluorescent image signal into several groups to calculate an average value of brightness levels of the pixels in each of the groups, calculates a difference between the average value of a group in the reference image signal and the average value of a group at the corresponding position in the fluorescent image signal for every group and generates an observation image signal by converting the pixels in the groups in the reference image signal whose difference is larger than the threshold value into specific pixels exhibiting a predetermined color; a memory section that stores the observation image signal and updates it whenever the observation image signal generating section generates an observation image signal; and an output section that reads the image signal stored in the memory section and that converts the image signal into an output video signal.

With this construction, when the number of pixels having the maximum brightness level in the reference image signal is larger than the threshold number, the reference image signal and the fluorescent image signal are divided into several groups, respectively, to calculate an average value of brightness levels of the pixels in each of the groups, and a difference between the average value of a group in the reference image signal and the average value of a group at the corresponding position in the fluorescent image signal is calculated for every group. This reduces the number of pixels for calculating the differences, which shorten a time required for differential process.

When the number of pixels having the maximum brightness level exceeds the threshold number, it can be judged that the endoscope does not focus on the subject and the contrast is low. That is, the tip of the endoscope should be moved to bring the subject in focus.

In such a case, since the number of the target pixels is reduced, the speed for generating the observation image signal increases, which enables to display the observation image signal on a monitor in real time during the movement. Therefore, an operator has little possibility to lose sight of an attention part.

On the contrary, when the number of pixels having the maximum value in the reference image signal does not exceed the threshold number, it can be judged that the endoscope focuses on the subject with high contrast.

In such a case, since all of the pixels are used as the target pixels for calculating the differences, the resolution increases while the speed for generating the observation image signal decreases, which enables detail observation of the subject by the operator.

DESCRIPTION OF THE ACCOMPANYING DRAWINGS

DESCRIPTION OF THE EMBODIMENTS

Embodiments of the present invention will be described hereinafter with reference to the drawings.

First Embodiment

Figure 1:
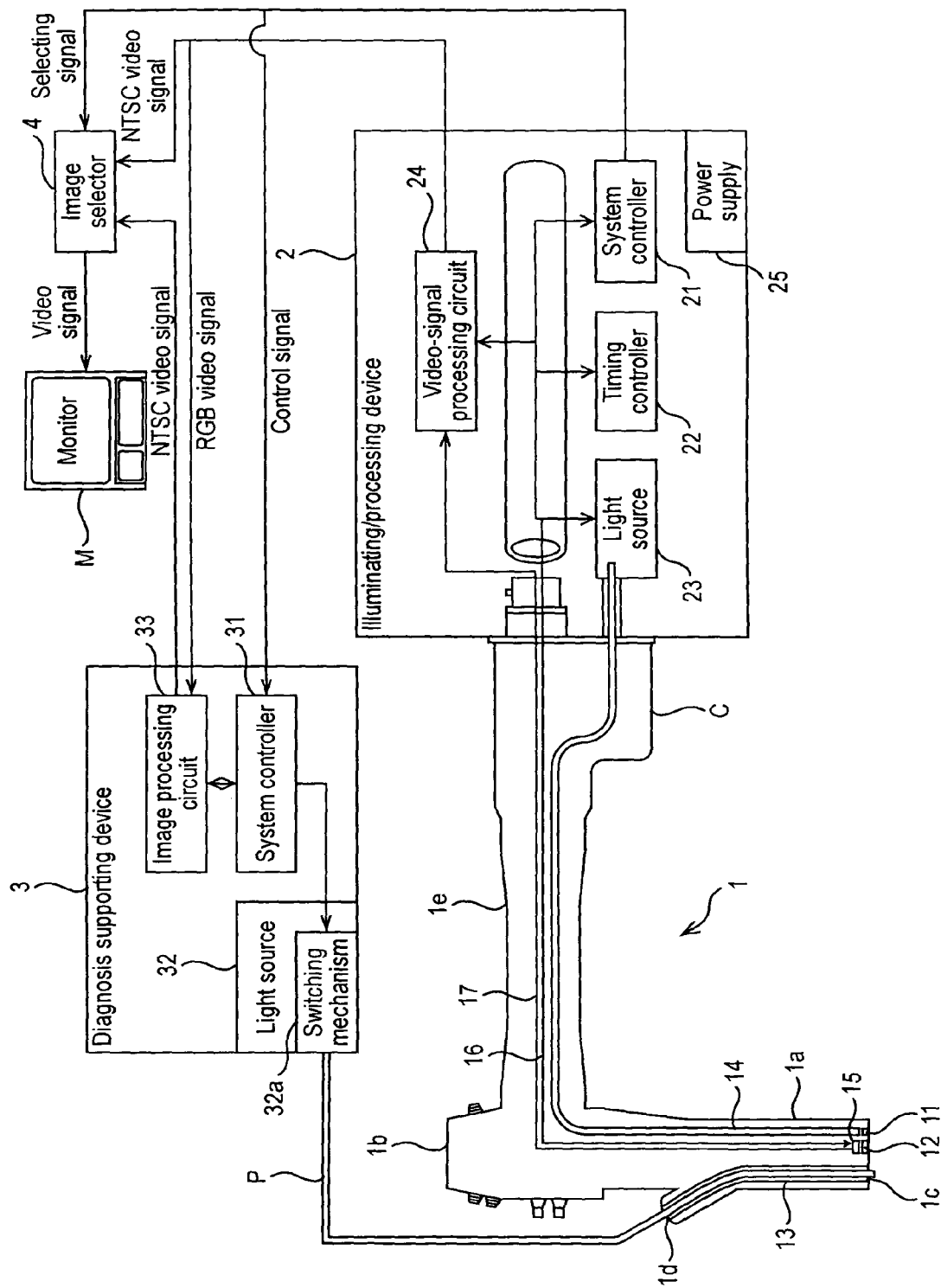
FIG. 1 is a block diagram showing an endoscope system of a first embodiment according to the present invention.

FIG. 1 is a block diagram of an endoscope system of the first embodiment. The endoscope system is provided with a video endoscope 1, an illuminating/processing device 2, a diagnosis supporting device 3, an image selector 4 and a monitor M.

At first, the video endoscope 1 will be explained. The video endoscope 1 has a flexible insertion tube 1a that can be inserted in a living body and an operating portion 1b on which angle knobs (not shown) to control a bending mechanism (not shown) built in the tip of the insertion tube 1a are mounted. A distribution lens 11 and an objective lens 12 are built on the tip surface of the insertion tube 1a and a forceps opening 1c of a forceps channel 13 opens at the tip surface. The other forceps opening 1d of the forceps channel 13 opens at the side of the operating portion 1b. A treatment tool such as an electric scalpel may be inserted through the forceps channel 13.

An image of a subject formed by the objective lens 12 is taken by an image sensor 15. A light guide 14 for transmitting light to the distribution lens 11 and signal lines 16 and 17 connected to the image sensor 15 are led through the insertion tube 1a.

The light guide 14 and the signal lines 16 and 17 are also led through a flexible tube 1e that is extended from the side of the operating portion 1b, and proximal ends thereof are fixed to an end face of a connector C mounted on the base of the flexible tube 1e.

Next, the illuminating/processing device 2 will be explained. The illuminating/processing device 2 includes a system controller 21, a timing controller 22, a light source 23, a video-signal processing circuit 24 and a power supply 25 supplying these circuits with electricity. Further, the illuminating/processing device 2 is provided with a connector-supporting portion (not show) to which the above-described connector C is fitted. Fitting the connector C to the connector-supporting portion, the proximal end of the light guide 14 is inserted into the light source 23 and the signal lines 16 and 17 are connected to the system controller 21 and the video-signal processing circuit 24.

The system controller 21 controls the entire system of the illuminating/processing device 2. The system controller 21 sets an observation mode in a first observation mode or a second observation mode in response to an operation of a switch mounted on an operation panel (not shown). The system controller 21 sends out a signal representing the first observation mode in the first observation mode and a signal representing the second observation mode in the second observation mode to the light source 23, the video-signal processing circuit 24 and the image selector 4, respectively.

Further, the system controller 21 sends out a driving signal to the image sensor 15 through the signal line 16 in any observation mode.

The timing controller 22 generates various reference signals and controls the outputs of them. Various processes in the illuminating/processing device 2 are executed according to the reference signals.

The light source 23 does not emit in the second observation mode while it repeatedly and sequentially emits red light, green light and blue light to be incident on the proximal end of the light guide 14 in the first observation mode. Incident light of each color is guided by the light guide 14 and is diffused by the distribution lens 11 to illuminate the subject faced to the tip of the video endoscope 1. Then, an image of the subject by red light, an image of the subject by green light and an image of the subject by blue light are sequentially formed on the image-taking surface of the image sensor 15.

The image sensor 15 converts the images of the subject formed by red, green and blue lights into the image signals, which are referred to as a red image signal, a green image signal and a blue image signal, respectively, sending the converted image signals to the video-signal processing circuit 24 through the signal line 17. The video-signal processing circuit 24 acquires a red image signal, a green image signal and a blue image signal, composing them to obtain a color image signal of the subject. In other words, the color image signal is acquired by a so-called frame-sequential method.

The video-signal processing circuit 24 converts the acquired color image signals into an RGB video signal, and then, converting the RGB video signal into an NTSC video signal or a PAL video signal. The video-signal processing circuit 24 sends out the NTSC video signal to the image selector 4 in the first observation mode and sends out the RGB video signal to the diagnosis supporting device 3 in the second observation mode without sending out the NTSC video signal to the image selector 4.

Next, the diagnosis supporting device 3 will be described. The diagnosis supporting device 3 is provided with a probe P, a system controller 31, a light source 32 and an image processing circuit 33.

The probe P is multiple flexible optical fibers bundled with one another or a single flexible optical fiber through which ultraviolet light of a predetermined band (excitation light) can transmit. The excitation light excites living tissue, which causes living tissue to emit fluorescence. Further, the probe P is led through the forceps channel 13 of the video endoscope 1.

The system controller 31 controls the entire system of the diagnosis supporting device 3. The system controller 31 is connected to the system controller 21 of the illuminating/processing device 2 and receives a control signal from the system controller 21 in the second observation mode. The control signal represents timings when the video-signal processing circuit 24 of the illuminating/processing device 2 periodically receives a red image signal, a green image signal and a blue image signal.

The light source 32 is provided with a lamp (not shown) to emit white light including visible light and excitation light, and a switching mechanism 32a including a shutter and filters that alternately extract visible light and excitation light from white light emitted from the lamp to make the extracted light be incident on the proximal end of the probe P.

The light source 32 is connected to the system controller 31, receiving the control signal from the system controller 31 in the second observation mode. Then, the light source 32 controls the switching mechanism 32a according to the control signal. For example, the light source 32 makes the visible light and the excitation light be incident on the proximal end of the probe P by turn in response to the timings when the video-signal processing circuit 24 receives the red image signal and the green image signal, respectively.

Facing the tip end of the probe P to a subject such as living tissue, the subject is alternately irradiated with the visible light and the excitation light guided through the probe P. The visible light illuminates the subject and the excitation light excites the subject to emit fluorescence.

The image sensor 15 converts an image of the subject illuminated by the visible light and an image of the subject formed by the fluorescence into respective image signals (referred to as a reference image signal and a fluorescence image signal, respectively), sending out these image signals to the video-signal processing circuit 24 through the signal line 17.

In the second observation mode, the video-signal processing circuit 24 acquires the reference image signal at the timing of receiving the red image signal (R-component) and acquires the fluorescent image signal at the timing of receiving the green image signal (G-component). Then, the video-signal processing circuit 24 sends out an RGB video-signal whose R-component represents the reference image signal and whose G-component represents the fluorescent image signal to the image processing circuit 33.

The image processing circuit 33 generates an observation image signal that is used in a diagnosis of a subject such as living tissue based on the RGB video signal transmitted from the video-signal processing circuit 24.

Figure 2:
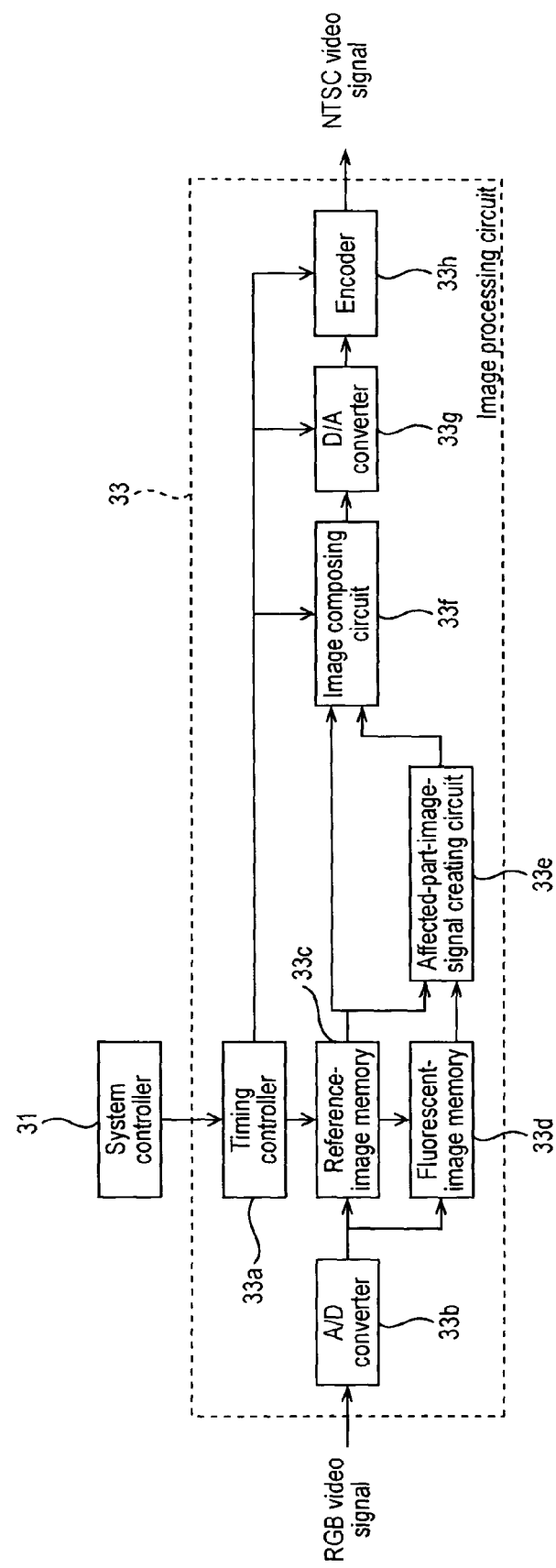
FIG. 2 is a block diagram showing an image processing circuit of a diagnosis supporting device shown in FIG. 1.

FIG. 2 shows an internal construction of the image processing circuit 33. As shown in FIG. 2, the image processing circuit 33 includes a timing controller 33a, an A/D converter 33b, a reference-image memory 33c, a fluorescent-image memory 33d, an affected-part-image-signal creating circuit 33e, an image composing circuit 33f, a D/A converter 33g and an encoder 33h.

Further, the A/D converter 33b, the reference-image memory 33c and the fluorescent-image memory 33d are equivalent to the image signal acquiring section. Still further, the affected-part-image-signal creating circuit 33e and the image composing circuit 33f are equivalent to the observation image signal generating section and the memory section. Furthermore, the D/A converter 33g and the encoder 33h are equivalent to the output section.

The timing controller 33a generates various reference signals based on the above control signal and controls the outputs of them. Various processes in the image processing circuit 33 are executed according to the reference signals.

The A/D converter 33b is connected to the video-signal processing circuit 24 of the illuminating/processing device 2, converting the analog RGB video signal fed from the video-signal processing circuit 24 into a digital signal.

Both the reference-image memory 33c and the fluorescent-image memory 33d are connected to the A/D converter 33b. The reference-image memory 33c stores the R-component of the digital RGB signal and the fluorescent-image memory 33d stores the G-component thereof. Therefore, the reference image signal based on the reference-image signal and the fluorescent image signal based on the fluorescent-image signal are temporally stored in the reference-image memory 33c and the fluorescent-image memory 33d, respectively.

The reference-image memory 33c outputs the reference image signal to the affected-part-image-signal creating circuit 33e and the image composing circuit 33f at a timing defined by the reference signal from the timing controller 33a.

Further, the fluorescent-image memory 33d outputs the fluorescent image signal to the affected-part-image-signal creating circuit 33e at the same timing when the reference-image memory 33c outputs the reference image signal.

The affected-part-image-signal creating circuit 33e has a ROM in which a program discussed below is stored, a CPU that executes the program read from the ROM, a RAM on which workspace of the CPU is developed and ports through which various signals and data for processing of the CPU are input/output. This affected-part-image-signal creating circuit 33e generates affected-part image signal based on the reference image signal and the fluorescent image signal, sending out the generated data to the image composing circuit 33f. Further, the CPU of the affected-part-image-signal creating circuit 33e executes processes according to programs read from the ROM while a main power supply keeps ON. Contents of the process will be described with reference to in FIG. 3 and FIG. 4.

Figure 3:
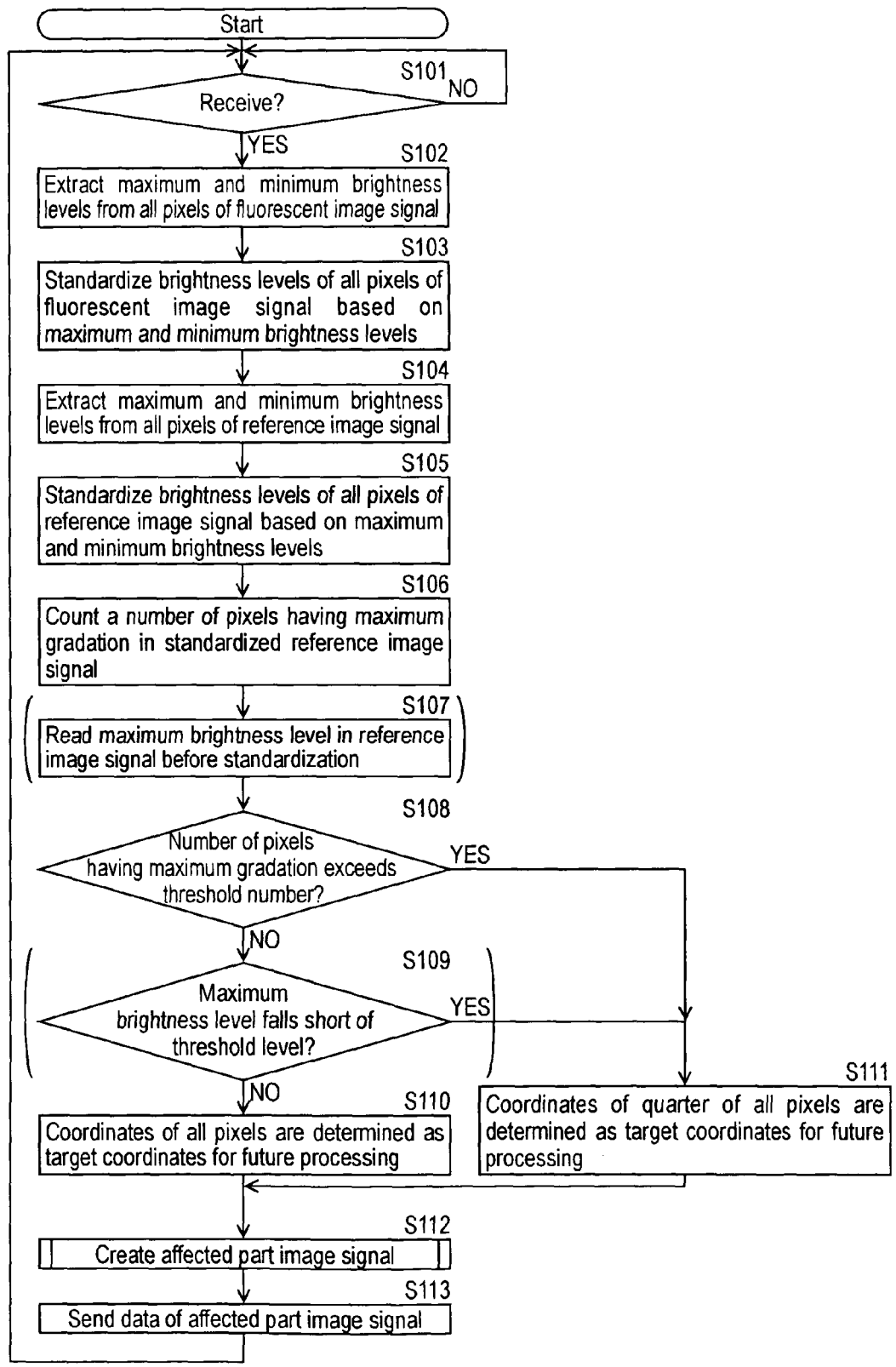
FIG. 3 is a flowchart to show a process of the first embodiment executed by an affected-part-image-signal creating circuit in the image processing circuit.

As shown in FIG. 3, the CPU waits receiving of reference image signal and fluorescent image signal transmitted from the respective memories 33c and 33d (S101).

When the CPU receives both the image signal, the CPU retracts the maximum and minimum brightness levels from all the pixels of the fluorescent image signal (S102).

Then the CPU standardizes brightness levels of all pixels in the fluorescent image signal by converting the maximum brightness level into the maximum gradation (for example, "255"), the minimum brightness level into the minimum gradation (for example, "0") and intermediate brightness levels into the respective corresponding gradations (S103). A gradation of a pixel is equivalent to a standardized brightness level.

Next, the CPU extracts the maximum and the minimum brightness levels from all the pixels of the reference image signal (S104).

Next, the CPU standardizes the brightness levels of all pixels in the reference image signal in the same manner as the process at S103 (S105).

Next, the CPU counts the number of pixels having the maximum gradation ("255" in this example) from all the pixels of the standardized reference image signal (S106) and reads the maximum brightness level from all pixels of the reference image signal before the standardization (S107).

The CPU judges whether the number of pixels having the maximum gradation counted at S106 exceeds a predetermined threshold number ("2000", for example) or not (S108).

Further, the CPU judges whether the maximum brightness level read at S107 falls short of a predetermined threshold level (for example, "150" when the range of the brightness level is "0 through 255") or not (S109).

Then, the CPU determines coordinates (x, y) of all pixels mapped on an x-y coordinate system with a horizontal x-axis and a vertical y-axis whose origin (0, 0) is located at the upper left endpoint as target coordinates for future processing (S110), when the number of pixels having the maximum gradation is smaller than the threshold number and the maximum brightness level exceeds the threshold level (S108: NO and S109: NO).

On the other hand, when the number of the pixels having maximum gradation exceeds the threshold number (S108: YES) or when the maximum brightness level is smaller than the threshold level (S109: YES), the CPU determines coordinates (2n, 2m) as the target coordinates for future processing (S111). Where n=0, 1, 2, . . . and m=0, 1, 2, . . .

The CPU executes an affected-part-image-signal creating subroutine (S112) after the CPU determines the target coordinates for future processing at S110 or S111. Contents of the affected-part image signal creating subroutine are shown in FIG. 4.

Figure 4:
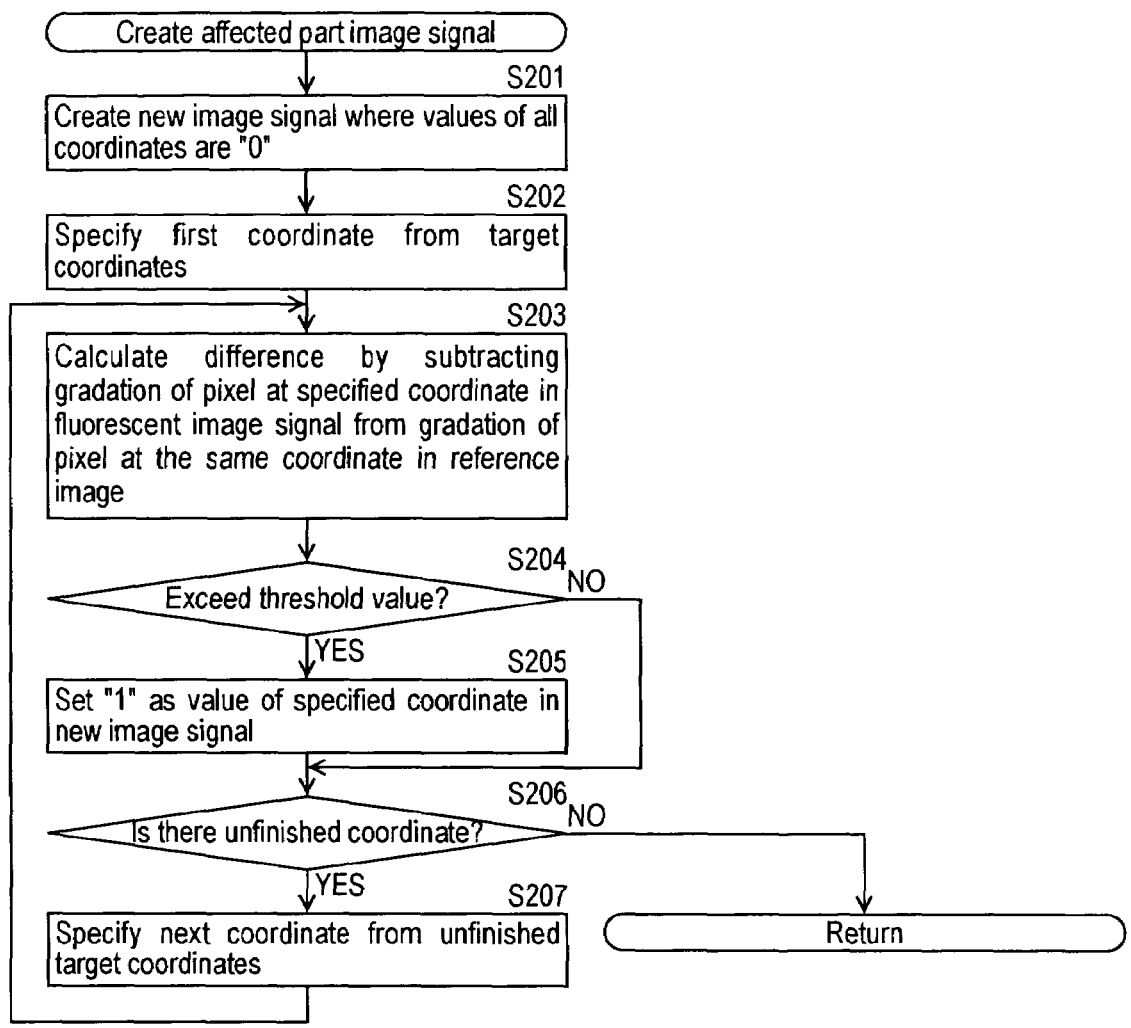
FIG. 4 is a flowchart to show an affected-part-image-signal creating subroutine of the first embodiment executed by the affected-part-image-signal creating circuit.

As shown in FIG. 4, the CPU creates a new image signal where values of all coordinates are "0" in the above coordinate system (S201), specifying the first coordinate from the target coordinates determined at S110 or S111 (S202).

Next, the CPU calculates a difference by subtracting the gradation (standardized brightness level) of the pixel at the specified coordinate in the standardized fluorescent image signal from the gradation (standardized brightness level) of the pixel at the same coordinate in the standardized reference image signal (S203), and the CPU judges whether the difference at the specific coordinate exceeds a predetermined threshold value or not (S204).

When the difference at the specified coordinate is equal to or larger than the threshold value (S204, YES), the CPU converts a pixel value on the coordinate in the new image signal generated at S201 into "1" from "0" (S205). When the difference is smaller than the threshold value (S204, NO), the pixel value on the coordinate in the new image signal remains at "0".

In other words, the new image signal is processed according to the algorithm so as to be an affected-part image signal showing the position and the shape of the affected part. Then, the CPU judges whether there is any unfinished coordinate in the target coordinates determined at S110 or S111 or not (S206).

When there is any unfinished coordinate (S206, YES), the CPU specifies a next coordinate from unfinished target coordinates (S207) and calculates a difference at the specified coordinate (S203).

If the differences are calculated for all the target coordinates by repeating the loop process S203 through S207 (S206, NO), the CPU finishes the affected-part-image-signal creating subroutine and returns the process back to S113 in the main routine shown in FIG. 3.

After finishing the affected-part-image-signal creating subroutine (S112), the CPU transmits the image signal of the affected-part image signal generated at S112 to the image composing circuit 33f as the affected-part image signal (S113). Then the CPU waits receiving of new reference image signal and new fluorescent image signal transmitted from the reference-image memory 33c and the fluorescent-image memory 33d (S101).

The CPU executes the process at S101 after transmitting the image signal to the image composing circuit 33f at S113. Therefore, the CPU does not accept reference image signal and fluorescent image signal during the process at S102 through S113 even if the image signal is transmitted from the memories 33c and 33d. This causes variation of performance for processing the reference image signal and the fluorescent image signal in response to the processing speed for the process at S102 through S113. That is, the faster the processing speed for the process at S102 through S113 is, the more the image signal can be processed and the more the can be generated.

Further, the reference image signal and the fluorescent image signal, which were not accepted by the CPU, are not used to generate an observation image signal.

According to the above process, the affected-part-image-signal creating circuit 33e generates the affected-part image signal as a binary image signal and transmits it to the image composing circuit 33f whenever reference image signal and fluorescent image signal sent from the respective memories 33c and 33d are received.

The image composing circuit 33f shown in FIG. 2 composes the affected image signal with the reference image signal that is the base for creating the affected-part image signal to generate observation image signal.

Specifically, the image composing circuit 33f generates a monochromatic RGB image signal with using the reference image signal when the reference image signal that is the base for creating the affected-part image signal is fed from the reference-image memory 33c. If the reference image signal that does not become a base of the affected-part image signal is input, it is not accepted by the image composing circuit 33f.

Further, when the affected-part image signal is fed from the affected-part-image-signal creating circuit 33e, the image composing circuit 33f generates an observation image signal by converting the pixels in the monochromatic RGB image signal at the same coordinates of the pixels in the affected-part image signal whose values are equal to "1" into specific pixels exhibiting a predetermined color (for example, red pixels whose RGB value is (255, 0, 0)).

Further, the image composing circuit 33f includes a buffer, which is equivalent to the memory section, to record image signal of the observation image signal. Whenever an observation image signal is generated, image signal recorded in the buffer is updated. Then, the image composing circuit 33f reads image signal from the buffer and sends it out to the D/A converter 33g according to the reference signal from the timing controller 33a (at the output timing of the NTSC video signal). The D/A converter 33g converts a digital signal representing the observation image signal into an analog RGB video signal.

The encoder 33h is connected to the D/A converter 33g, converting an input RGB video signal into an NTSC video signal (or a PAL video signal) to outputs it for the image selector 4.

Next, the image selector 4 will be described. As described above, the image selector 4 receives the signal representing the first observation mode or the signal representing the second observation mode from the system controller 21 of the illuminating/processing device 2.

The image selector 4 selects the NTSC video signal that is fed from the video-signal processing circuit 24 of illuminating/processing device 2 to output it to the monitor M to display a full-color observation image signal in the first observation mode.

On the other hand, the image selector 4 outputs the NTSC video signal that is fed from the image processing circuit 33 of the diagnosis supporting device 3 to the monitor M to display a two-color observation image signal (a monochrome-red image signal) based on the NTSC video signal on the monitor M in the second observation mode.

Next, the operation of the first embodiment will be described. An operator inserts the insertion tube 1a of the video endoscope 1 into a body cavity, directing the tip end to a subject to be observed. Then the operator flips a switch on an operation panel (not shown) of the illuminating/processing device 2 to change the observation mode to the first observation mode. Then, the monitor M displays a full-color image signal of the area faced to the tip end of the video endoscope 1. The operator can observe the subject with viewing the color image signal.

Furthermore, the operator observes the area, which is selected through the observation of the color image signal, with the aid of the diagnosis supporting device 3. Specifically, the operator inserts the probe P of the diagnosis supporting device 3 into the forceps channel 13 from the forceps opening 1d of the video endoscope 1 so that the tip of the probe P projects juts from the forceps opening 1c at the tip side.

In addition, the operator flips the switch on the operation panel (not shown) of the illuminating/processing device 2 to change the observation mode to the second observation mode. Then visible light and excitation light are emitted in turn from the tip of the probe P. The video endoscope 1 alternately takes the body cavity wall illuminated by the visible light and the body cavity wall that emits fluorescence.

As a result, the video-signal processing circuit 24 of the illuminating/processing device 2 in the second observation mode outputs an RGB video signal including a reference image signal and a fluorescent image signal to the image processing circuit 33 of the diagnosis supporting device 3.

In the image processing circuit 33 that receives the RGB video signal, the affected-part-image-signal creating circuit 33e generates an affected-part image signal based on the reference image signal and the fluorescent image signal, and the image composing circuit 33f generates an observation image signal.

As described above, the observation image signal is generated by converting the pixels of the monochromatic RGB image signal based on the reference image signal at the same coordinates of the pixels in the affected-part image signal whose values are equal to "1" into the red pixels.

While the image selector 4 receives the signal representing the second observation mode, the image selector 4 selects an NTSC video signal fed from the image processing circuit 33 to output it to the monitor M. Therefore, the observation image signal is displayed on the monitor M in the second observation mode.

The positions of the red pixels in the observation image signal displayed on the monitor M are coincident with the coordinates of pixels having value "1" in the affected-part image signal. Further, the coordinates of the pixels having value "1" show the coordinates having large brightness levels in the reference image signal and small brightness levels in the fluorescent image signal. That is, the coordinates of the pixels having value "1" show the relatively near areas to which certain amount of the visible light is illuminated and from which weak fluorescence emits under irradiation with the excitation light.

Since intensity of fluorescence emitted from abnormal living tissue that is suffering from a lesion such as a tumor or cancer is smaller than that emitted from normal living tissue, the red pixels show the parts that can be judged as affected parts.

Therefore, an operator can specify an outline and unevenness of body cavity wall through a monochromatic part in the observation image signal and can specify parts that have high risk to be suffering from a lesion such as a tumor or cancer through maculate red parts and/or block red parts in the observation image signal.

When a taking area of the video endoscope 1 changes while body cavity wall is observed, the processing speed may be insufficient for change of the taking area.

For example, when the video endoscope 1 cannot focus on body cavity wall, contrast of a monochromatic part in an observation image signal (a monochromatic RGB reference image signal) may extremely deteriorate, which makes the almost entire area of the monochromatic part be in pure white or jet-black.

In the first embodiment, when the number of pixels having the maximum gradation in the standardized reference image signal exceeds the predetermined threshold number, it is judged that the almost entire area of the monochrome part of the observation image signal is in pure white.

On the other hand, when the maximum brightness level in the reference image signal before standardization falls short of the predetermined threshold level, it is judged that the almost entire area of the monochromatic part of the observation image signal is in jet-black.

In either case, since the contrast becomes too low to observe the subject, the operator must move the tip end of the video endoscope 1 to catch the subject in focus.

In such a case, the affected-part-image-signal creating circuit 33e reduces the number of the target coordinates to ¼ of all coordinates (S108 through S111). Herewith a time needed to create an affected-part image signal becomes about half (it should be ¼ in theory, but about half in fact) as compared with the case when all coordinates are defined as the target coordinates. That is, the speed for creating an affected-part image signal is twice as fast as the case when all coordinates are defined as the target coordinates.

Therefore, the observation image signal can be displayed on the monitor M in real time during the movement when the operator moves the tip of the video endoscope 1. Accordingly, the operator has little possibility to lose sight of an attention part.

On the contrary, when the number of pixels having the maximum gradation in the standardized reference image signal does not exceed the threshold number and the maximum brightness level in the reference image signal before standardization exceeds the threshold level, the affected-part-image-signal creating circuit 33e judges that the endoscope focuses on the subject with high contrast, defining all the coordinates as the target coordinates for creating an affected-part image signal.

In such a case, the resolution increases while the speed for generating the observation image signal decreases, which enables detail observation of the subject by the operator.

Further, in the first embodiment, the process at S108 judges whether almost entire area in the reference image signal is in pure white or not and the process at S109 judges whether almost entire area in the reference image signal is in jet-black or not. However, the judgement at S109 maybe eliminated. In this case, the process at S107 is also unnecessary.

Second Embodiment

A video endoscope system of a second embodiment will be explained next.

A system configuration of the second embodiment is the same as the first embodiment except a few differences of process contents executed in the affected-part-image-signal creating circuit 33e (that is, a slightly different program is stored in the ROM). In the second embodiment, the definition of the target coordinates for creating a next affected-part image signal is decided based on the number of pixels having value "1" in the current affected-part image signal.

Hereinafter, the process contents in the affected-part-image-signal creating circuit 33e that are differences from the first embodiment will be described.

Figure 5:
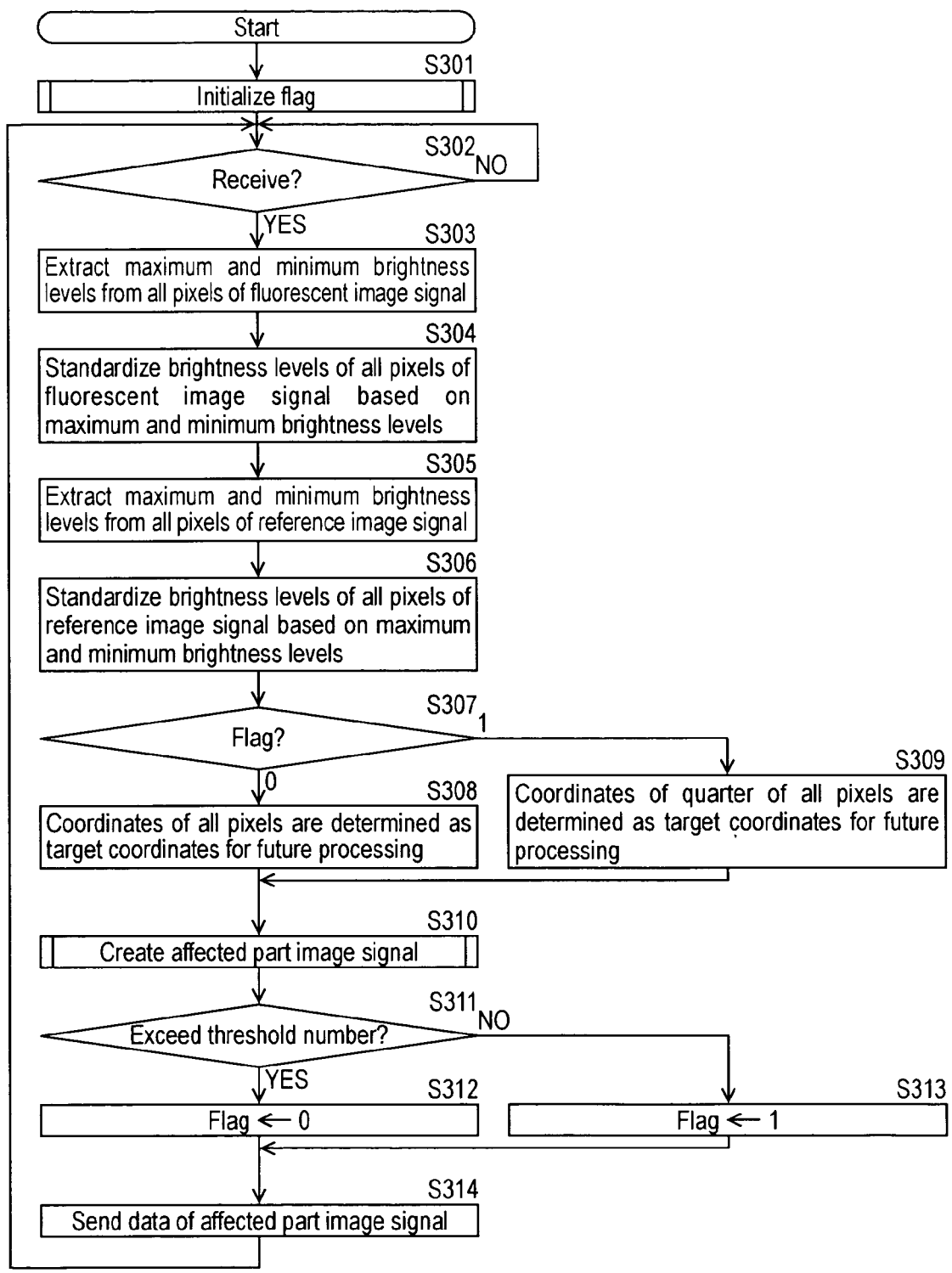
FIG. 5 is a flowchart to show a process of a second embodiment executed by the affected-part-image-signal creating circuit.

FIG. 5 is a flowchart showing the process contents executed by the affected-part-image-signal creating circuit 33e of the second embodiment.

As shown in FIG. 5, the CPU substitutes "0" into a flag that indicates whether the target coordinates are reduced or not and records it into the RAM (equivalent to an information register) to initialize the flag (S301).

Further, the processes at S302 through S306 are identical to the processes at S101 through S105 shown in FIG. 3. That is, the CPU standardizes all pixels in a fluorescent image signal and all pixels in a reference image signal (S302 through S306).

And then, the CPU distinguishes whether the flag at the present is "0" or "1" (S307). When the flag is "0" (S307, "0"), the CPU determines coordinates (x, y) of all pixels mapped on an x-y coordinate system with a horizontal x-axis and a vertical y-axis whose origin (0, 0) is located at the upper left endpoint as target coordinates for future processing (S308).

On the other hand, when the flag is "1" (S307, 1), the CPU determines coordinates (2n, 2m) as the target coordinates for future processing (S309). Where n=0, 1, 2, . . . and m=0, 1, 2, . . . .

The CPU executes an affected-part-image-signal creating subroutine (S310) after the CPU determines the target coordinates for future processing at S308 or S309.

After finishing the affected-part-image-signal creating subroutine, the CPU distinguishes whether the number of pixels having value "1" in the created affected-part image signal exceeds a predetermined threshold number (for example, the number equals 5% of the number of all pixels) or not (S311).

When the number of the pixels having value "1" exceeds the threshold number (S311, YES), the CPU substitutes "0" into the flag (S312).

On the other hand, when the number of the pixels having value "1" is smaller than the threshold number (S311, NO), the CPU substitutes "1" into the flag (S313).

After updating the flag at S312 or S313, the CPU transmits the image signal of the binary image signal generated at S310 to the image composing circuit 33f as an affected-part image signal (S314). Then the CPU waits receiving of new reference image signal and new fluorescent image signal transmitted from the reference-image memory 33c and the fluorescent-image memory 33d (S302).

As a result of the above-mentioned process executed in the affected-part-image-signal creating circuit 33e, the affected-part-image-signal creating circuit 33e decides that the image signal includes a part should be observed in detail, defining all coordinates as the target coordinates for creating a next affected-part image signal when the number of the specific pixels having value "1" exceeds the predetermined threshold number (S307, S308, S310 through S312 and S314).

On the other hand, when the number of the specific pixels having value "1" in the affected-part image signal does not exceed the predetermined threshold number, the affected-part-image-signal creating circuit 33e decides that the image signal does not include a part should be observed in detail, defining ¼ of all coordinates as the target coordinates for creating a next affected-part image signal (S307, S309, S311, S313 and S314). Further, the process at S311 through S313 represents an operation of the condition deciding section.

According to the second embodiment, when parts suffering from a lesion such as a tumor or cancer are not found, the speed for generating the observation image signal increases, which enables to display the observation image signal on the monitor M in real time. As a result, the operator has little possibility to lose sight of an attention part, which prevents a delay of an operation.

On the other hand, when the observed area has high risk to be suffering from a lesion, the resolution increases while the speed for generating the observation image signal decreases, which enables detail observation of the subject by the operator.

Third Embodiment

A video endoscope system of a third embodiment will be described next.

A system configuration of the third embodiment is the same as the first embodiment except a few difference of process contents executed in the affected-part-image-signal creating circuit 33e. In the third embodiment, when the reference image signal has low contrast, all pixels in each of the reference image signal and the fluorescent image signal are divided into several groups to calculate an average value of brightness levels of the pixels in each of the groups. An affected-part image signal is created based on a difference between the average value of a group in the reference image signal and the average value of a group at the corresponding position in the fluorescent image signal for every group.

Figure 6:
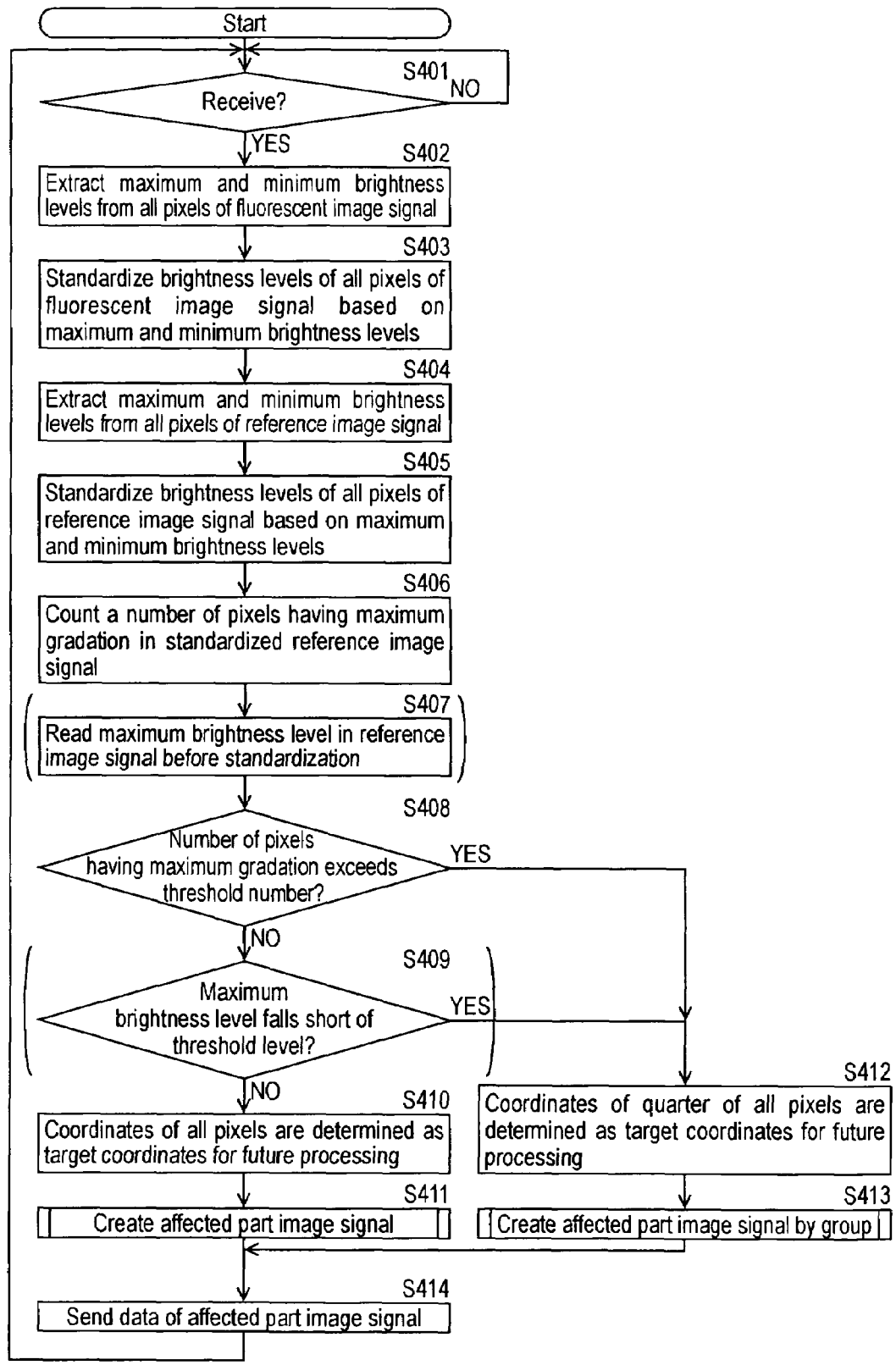
FIG. 6 is a flowchart to show a process of a third embodiment executed by the affected-part-image-signal creating circuit.

Hereinafter, the process contents in the affected-part-image-signal creating circuit 33e that are differences from the first embodiment will be described. FIG. 6 is a flowchart showing the process contents executed by the affected-part-image-signal creating circuit 33e of the third embodiments.

As shown in FIG. 6, the processes at S401 through S409 are identical to the processes at S101 through S109 shown in FIG. 3. That is, the CPU standardizes all pixels in a fluorescent image signal and all pixels in a reference image signal (S401 through S405), counts the number of the pixels having the maximum gradation from all the pixels of the standardized reference image signal (S406) and reads the maximum brightness level from all pixels of the reference image signal before the standardization (S407).

Then, the CPU judges whether the number of pixels having the maximum gradation counted at S406 exceeds a predetermined threshold number or not (S408).

Further, the CPU judges whether the maximum brightness level read at S407 falls short of a predetermined threshold level or not (S409).

Then, the CPU determines coordinates (x, y) of all pixels mapped on an x-y coordinate system with a horizontal x-axis and a vertical y-axis whose origin (0, 0) is located at the upper left endpoint as target coordinates for future processing (S410) and executes the affected-part-image-signal creating subroutine shown in FIG. 4 (S411), when the number of pixels having the maximum gradation is smaller than the threshold number and the maximum brightness level exceeds the threshold level (S408: NO and S409: NO).

On the other hand, when the number of the pixels having maximum gradation exceeds the threshold number (S408: YES) or when the maximum brightness level is smaller than the threshold level (S409: YES), the CPU determines coordinates (2n, 2m) as the target coordinates for future processing (S412). Where n=0, 1, 2, . . . and m=0, 1, 2, . . . .

Figure 7:
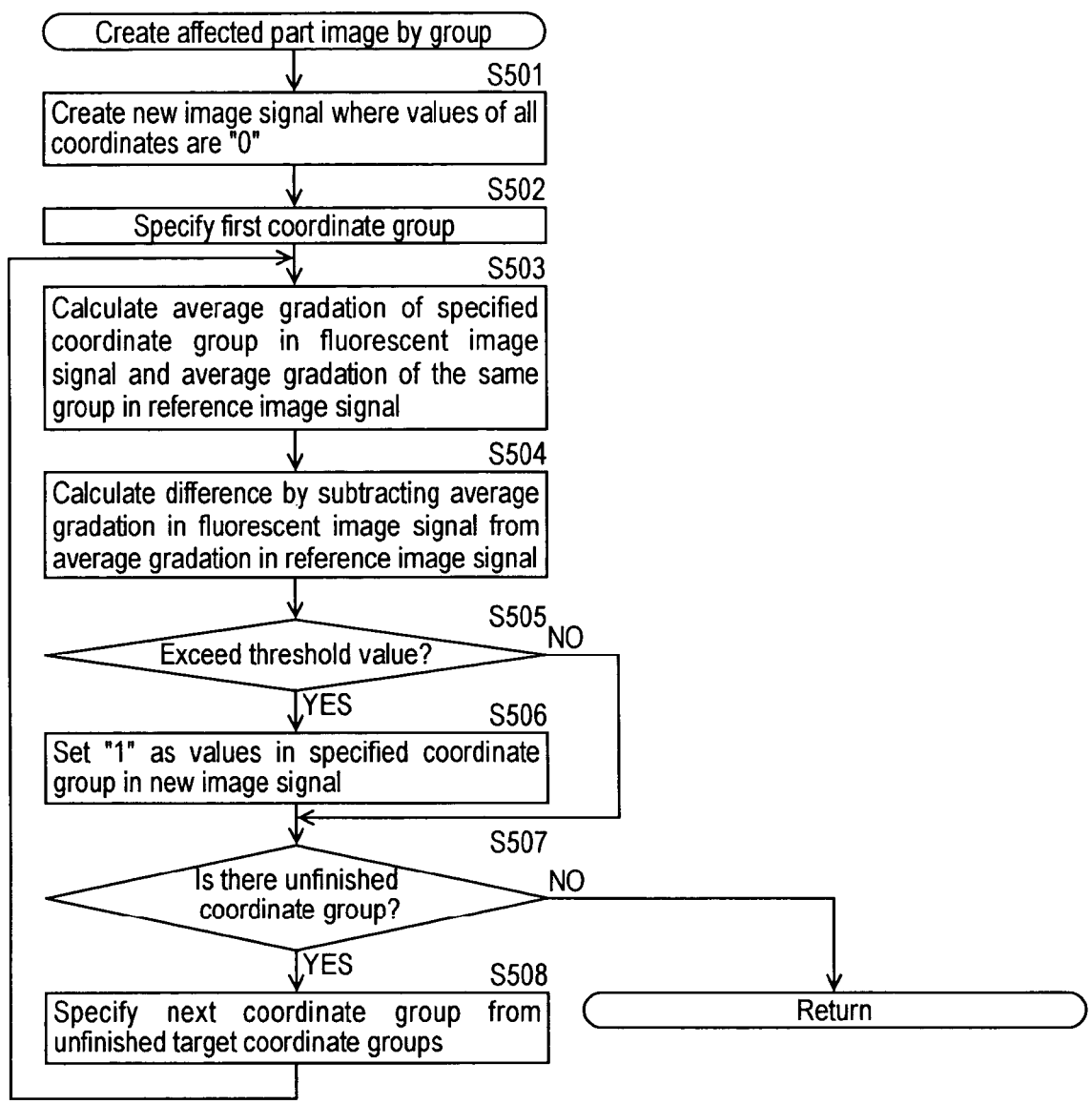
FIG. 7 is a flowchart to show an affected-part-image-signal creating subroutine of the third embodiment executed by the affected-part-image-signal creating circuit.

The CPU executes an affected-part-image-signal creating subroutine for group shown in FIG. 7 (S413).

As shown in FIG. 7, in the affected-part-image-signal creating subroutine for group, the CPU creates a new image signal where values of all coordinates are "0" in the above coordinate system (S501), specifying a first coordinate group (S502). The first coordinate group consists the first coordinate (2n, 2m) specified from the target coordinates determined at S412 and three coordinates (2n, 2m+1), (2n+1, 2m) and (2n+1, 2m+1) adjacent to the specified coordinate (2n, 2m).

Next, the CPU calculates the average value of the gradations at the above four coordinates in the standardized reference image signal and the average value of the gradations at the same four coordinates in the standardized fluorescent image signal (S503). Then, the CPU calculates a difference by subtracting the average gradation of the four coordinates in the standardized fluorescent image signal from the average gradation of the same four coordinates in the standardized reference image signal (S504), and the CPU judges whether the difference at the specific coordinate group exceeds a predetermined threshold value or not (S505).

When the difference at the specified coordinate group is equal to or larger than the threshold value (S505, YES), the CPU converts pixel values on the four coordinates in the new image signal generated at S501 into "1" from "0" (S506). When the difference is smaller than the threshold value (S505, NO), the pixel values on the four coordinate in the new image signal remains at "0".

In other words, the new image signal is processed according to the algorithm so as to be an affected-part image signal showing the position and the shape of the affected part.

Then, the CPU judges whether there is any unfinished coordinate in the target coordinates determined at S412 or not (S507).

When there is any unfinished coordinate (S507, YES), the CPU specifies a next coordinate from unfinished target coordinates and determines the specified coordinate and the three coordinates adjacent to the specified coordinate as the target coordinate group for the next process loop (S508).

If the differences are calculated for all the target coordinates by repeating the loop process S503 through S508 (S507, NO), the CPU finishes the affected-part-image-signal creating subroutine for group and returns the process back to S414 in the main routine shown in FIG. 6.

After finishing the affected-part-image-signal creating subroutine (S411, FIG. 4) or the affected-part-image-signal creating subroutine for group (S413, FIG. 7), the CPU transmits the image signal of the affected-part image signal generated at S411 or S413 to the image composing circuit 33f as the affected-part image signal (S414). Then the CPU waits receiving of new reference image signal and new fluorescent image signal transmitted from the reference-image memory 33c and the fluorescent-image memory 33d (S401).

As a result of the above-mentioned process executed in the affected-part-image-signal creating circuit 33e, the affected-part-image-signal creating circuit 33e compares gradation of a pixel in the reference image signal with gradation of a pixel at the same coordinate in the fluorescent image signal (FIG. 4) when the observation is available. On the other hand, the affected-part-image-signal creating circuit 33e compares average gradation of pixel group in the reference image signal with average gradation of pixel group at the same coordinates in the fluorescent image signal (FIG. 7) when the observation is difficult.

According to the third embodiment, since the average gradations of the pixel groups are compared when the observation is difficult, the number of comparisons is reduced, which increases the speed for generating the observation image signal, enabling to display the observation image signal on the monitor M in real time.

As a result, the operator has little possibility to lose sight of an attention part, which prevents a delay of an operation.

On the other hand, when the observation is available, all the pixels become the target pixels, the resolution increases while the speed for generating the observation image signal decreases, which enables detail observation of the subject by the operator.

Further, in the third embodiment, the process at S408 judges whether almost entire area in the reference image signal is in pure white or not and the process at S409 judges whether almost entire area in the reference image signal is in jet-black or not. However, the judgement at S409 may be eliminated. In this case, the process at S407 is also unnecessary.

As described above, the present invention can provide an improved diagnosis supporting device that is capable of changing a processing speed corresponding to a condition of an input image.

The present disclosure relates to the subject matter contained in Japanese Patent Application No. P2002-287034, filed on Sep. 30, 2002, which are expressly incorporated herein by reference in its entirety.

What is claimed is:

1. A diagnosis supporting device that is connected to a processor device that acquires an image signal of an image of a subject formed at the tip of an endoscope to convert said image signal into an output video signal for a monitor, said diagnosis supporting device comprising:
   an image signal acquiring section that repeatedly acquires a reference image signal and a fluorescent image signal transmitted from said processor device, said reference image signal representing an image of a subject that is illuminated with visible light and said fluorescent image signal representing an image of said subject that is excited by irradiation with excitation light to emit fluorescence;
   an observation image signal generating section that counts the number of pixels having the maximum brightness level in said reference image signal whenever said image signal acquiring section acquires a set of said reference image signal and said fluorescent image signal, then that calculates a difference between brightness level of a pixel in said reference image signal and brightness level of a pixel in said fluorescent image signal at the corresponding position for all of the pixels in said reference image signal when the number of counted pixels is not larger than a predetermined threshold number or for a part of the pixels selected from said reference image signal when the number of counted pixels is larger than said threshold number, and that generates an observation image signal by converting the pixels in said reference image signal whose differences are larger than a predetermined value into specific pixels exhibiting a predetermined color;
   a memory section that stores the observation image signal and updates it whenever said observation image signal generating section generates an observation image signal; and
   an output section that reads said observation image signal stored in said memory section and that converts said observation image signal into an output video signal.

2. The diagnosis supporting device according to claim 1, wherein said observation image signal generating section calculates a difference between brightness level of a pixel in said reference image signal and brightness level of a pixel in said fluorescent image signal at the corresponding position for a part of the pixels selected from said reference image signal even when the maximum brightness in said reference image signal is smaller than a predetermined threshold level.

3. The diagnosis supporting device according to claim 1, wherein said observation image signal generating section standardizes brightness levels of all pixels in said reference image signal and said fluorescent image signal by converting the maximum brightness level into the maximum gradation, the minimum brightness level into the minimum gradation and intermediate brightness levels into the respective corresponding gradations, and then said observation image signal generating section counts the number of pixels having the maximum gradation in all the pixels of the standardized reference image signal.

4. The diagnosis supporting device according to claim 3, wherein said observation image signal generating section selects ¼ of all the pixels in said reference image signal as target pixels for calculating said difference when the number of the pixels having the maximum brightness level in said reference image signal is larger than said threshold number.

5. The diagnosis supporting device according to claim 1, wherein said observation image signal generating section generates said observation image signal by converting said reference image signal into a monochromatic RGB image signal after calculating said differences.

6. The diagnosis supporting device according to claim 1, wherein said specific pixels exhibit red.

7. The diagnosis supporting device according to claim 1, further comprising:
   a probe that is led through a forceps channel of said video endoscope to guide visible light for illuminating said subject and excitation light for exciting said subject to cause living tissue to emit fluorescence; and
   a light source that makes visible light and excitation light be alternately incident on the proximal end of said probe.

8. The diagnosis supporting device according to claim 7, wherein said probe consists of a number of optical fibers that are bundled up with one another.

9. A diagnosis supporting device that is connected to a processor device that acquires an image signal of an image of a subject formed at the tip of an endoscope to convert said image signal into an output video signal for a monitor, said diagnosis supporting device comprising:
   an image signal acquiring section that repeatedly acquires a reference image signal and a fluorescent image signal transmitted from said processor device, said reference image signal representing an image of a subject that is illuminated with visible light and said fluorescent image signal representing an image of said subject that is excited by irradiation with excitation light to emit fluorescence;
   an observation image signal generating section that counts the number of pixels having the maximum brightness level in said reference image signal whenever said image signal acquiring section acquires a set of said reference image signal and said fluorescent image signal, that calculates, when the number of counted pixels is not larger than a predetermined threshold number, a difference between brightness level of a pixel in said reference image signal and brightness level of a pixel in said fluorescent image signal at the corresponding position for all of the pixels in said reference image signal and generates an observation image signal by converting the pixels in said reference image signal whose differences are larger than a predetermined value into specific pixels exhibiting a predetermined color, and that divides, when the number of counted pixels is larger than said threshold number, all pixels in both of said reference image signal and said fluorescent image signal into several groups to calculate an average value of brightness levels of the pixels in each of the groups, calculates a difference between the average value of a group in said reference image signal and the average value of a group at the corresponding position in said fluorescent image signal for every group and generates an observation image signal by converting the pixels in the groups in said reference image signal whose difference is larger than said threshold value into specific pixels exhibiting a predetermined color;

a memory section that stores said observation image signal and updates it whenever said observation image signal generating section generates an observation image signal; and an output section that reads said image signal stored in said memory section and that converts said image signal into an output video signal.

10. The diagnosis supporting device according to claim 9, wherein said observation image signal generating section divides all pixels in each of said reference image signal and said fluorescent image signal into several groups to calculate an average value of brightness levels of the pixels in each of the groups, calculates a difference between the average value of a group in said reference image signal and the average value of a group at the corresponding position in said fluorescent image signal for every group and generates an observation image signal by converting the pixels in the groups in said reference image signal whose difference is larger than said threshold value into specific pixels exhibiting a predetermined color even when the maximum brightness level in said reference image signal is smaller than a predetermined threshold level.

11. The diagnosis supporting device according to claim 9, wherein said observation image signal generating section standardizes brightness levels of all pixels in said reference image signal and said fluorescent image signal by converting the maximum brightness level into the maximum gradation, the minimum brightness level into the minimum gradation and intermediate brightness levels into the respective corresponding gradations, and then said observation image signal generating section counts the number of pixels having the maximum gradation in all the pixels of the standardized reference image signal.

12. The diagnosis supporting device according to claim 11, wherein said observation image signal generating section selects ¼ of all the pixels in said reference image signal as target pixels for calculating said difference when the number of the pixels having the maximum brightness level in said reference image signal is larger than said threshold number.

13. The diagnosis supporting device according to claim 9, wherein said observation image signal generating section generates said observation image signal by converting said reference image signal into a monochromatic RGB image signal after calculating said differences.

14. The diagnosis supporting device according to claim 9, wherein said specific pixels exhibit red.

15. The diagnosis supporting device according to claim 9, further comprising:
    a probe that is led through a forceps channel of said video endoscope to guide visible light for illuminating said subject and excitation light for exciting said subject to cause living tissue to emit fluorescence; and
    a light source that makes visible light and excitation light be alternately incident on the proximal end of said probe.

16. The diagnosis supporting device according to claim 15, wherein said probe consists of a number of optical fibers that are bundled up with one another.

* * * * *